United States Patent

Gedeon et al.

[11] Patent Number: 5,299,579
[45] Date of Patent: Apr. 5, 1994

[54] APPARATUS FOR EXAMINING A PATIENT'S PULMONARY FUNCTION

[75] Inventors: Andras Gedeon, Täby; Claes Mebius, Djursholm, both of Sweden

[73] Assignee: MINCO AB, Taby, Sweden

[21] Appl. No.: 859,362

[22] PCT Filed: Nov. 23, 1990

[86] PCT No.: PCT/SE90/00770
§ 371 Date: May 26, 1992
§ 102(e) Date: May 26, 1992

[87] PCT Pub. No.: WO91/07912
PCT Pub. Date: Jun. 13, 1991

[30] Foreign Application Priority Data

Nov. 24, 1989 [SE] Sweden .................. 8903964

[51] Int. Cl.⁵ .................................. A61B 5/08
[52] U.S. Cl. .......................... 128/719; 128/718; 128/205.14; 128/205.15
[58] Field of Search .............. 128/718, 719, 205.14, 128/205.15

[56] References Cited

U.S. PATENT DOCUMENTS

| | | | |
|---|---|---|---|
| 2,592,694 | 4/1952 | Heidbrink | 128/718 |
| 3,527,205 | 9/1970 | Jones | 128/719 |
| 3,951,137 | 4/1976 | Conkle et al. | 128/719 |
| 4,231,362 | 11/1980 | Pearson et al. | 128/205.15 |
| 4,233,842 | 11/1980 | Raemer et al. | |
| 4,753,245 | 6/1988 | Gedeon | |
| 4,856,531 | 8/1989 | Merilainen | |
| 4,947,860 | 8/1990 | Fisher | 128/719 |
| 5,038,772 | 8/1991 | Kolbe et al. | 128/205.14 |
| 5,111,809 | 5/1992 | Gamble et al. | 128/205.14 |

FOREIGN PATENT DOCUMENTS 2425535 12/1975 Fed. Rep. of Germany .

Primary Examiner—Lee S. Cohen
Assistant Examiner—Brian L. Casler
Attorney, Agent, or Firm—Browdy and Neimark

[57] ABSTRACT

Apparatus for examining pulmonary function parameters of a patient comprises a rebreathing system (1–6) adapted to be connected with the patient and including a variable-volume reservoir (1), a carbon dioxide absorber (19) in an inhalation conduit (3) and valve means (24) for selectively switching the carbon dioxide absorber (19) on and off. A carbon dioxide meter (25) is controllable to selectively measure the carbon dioxide content of respiratory gas being exhaled and of exhaled respiratory gas collected in the reservoir (1). Volume monitoring devices (17,18) monitory the volume variations of the reservoir (1). A computing unit (30) computes the pulmonary blood flow and other pulmonary function parameters using carbon dioxide concentration parameters measured by the carbon dioxide meter (25) and ventilatory rate parameters are measured by the monitoring devices (17,18).

20 Claims, 3 Drawing Sheets

APPARATUS FOR EXAMINING A PATIENT'S PULMONARY FUNCTION

FIELD OF THE INVENTION

This invention relates to apparatus for non-invasively examining and measuring pulmonary function parameters of a patient. The apparatus has been developed primarily for measuring the pulmonary blood flow or perfusion, and simultaneous measurement of the carbon dioxide removal from the lungs and the pulmonary volume for carbon dioxide is possible. A further feature of the apparatus according to the invention makes it possible also to measure the oxygen consumption, the respiratory quotient and the oxygen saturation of the mixed venous blood.

BACKGROUND OF THE INVENTION

The pulmonary blood flow or pulmonary perfusion is the rate of flow of the blood passing through the lungs in gas-exchange relation with the respiratory gas contained in the alveoles of the lungs. It is to be noted that this rate of flow is not neccessarily equal to the rate of flow of the blood discharged from the heart, because defects in the blood circulation may result in less than the entire cardiac output reaching the lungs. Moreover, it is not neccessarily equal to the blood flow actually passing through the lungs, because defects of the lungs, such as clogged or collapsed alveols, may result in less than the total blood flow through the lungs coming into gas-exchange contact with the respiratory gas.

Accordingly, the pulmonary blood flow is a measure of the effectiveness of the pulmonary function and obviously is important to examine and measure in patients having an impaired pulmonary function and/or an impaired cardiac function. Of particular interest is the measurement of the pulmonary blood flow in patients having both an impaired pulmonary function and an impaired cardiac function, because many therapeutic methods for improving the pulmonary function impair the cardiac function.

Several different methods for determining the pulmonary blood flow have previously been proposed and have also been practised to some extent. These previously known methods are very complicated and time-consuming, however, and for that reason are not practically useful for clinical purposes. Besides, some of them are invasive. Certain of the previously known methods require that the patient be supplied with respiratory gas that includes non-physiological gases.

SUMMARY OF THE INVENTION

Accordingly, the object of the present invention is to provide simple and accurate apparatus for non-invasively measuring the pulmonary blood flow and other pulmonary function parameters of a patient without supplying non-physiological gases to the patient.

The characterising features of the invention are set forth in the accompanying claims.

BRIEF DESCRIPTION OF THE DRAWINGS

The invention will be described in greater detail hereinafter with references to the accompanying drawings, in which.

DETAILED DESCRIPTION OF THE DRAWINGS

Figure 1:
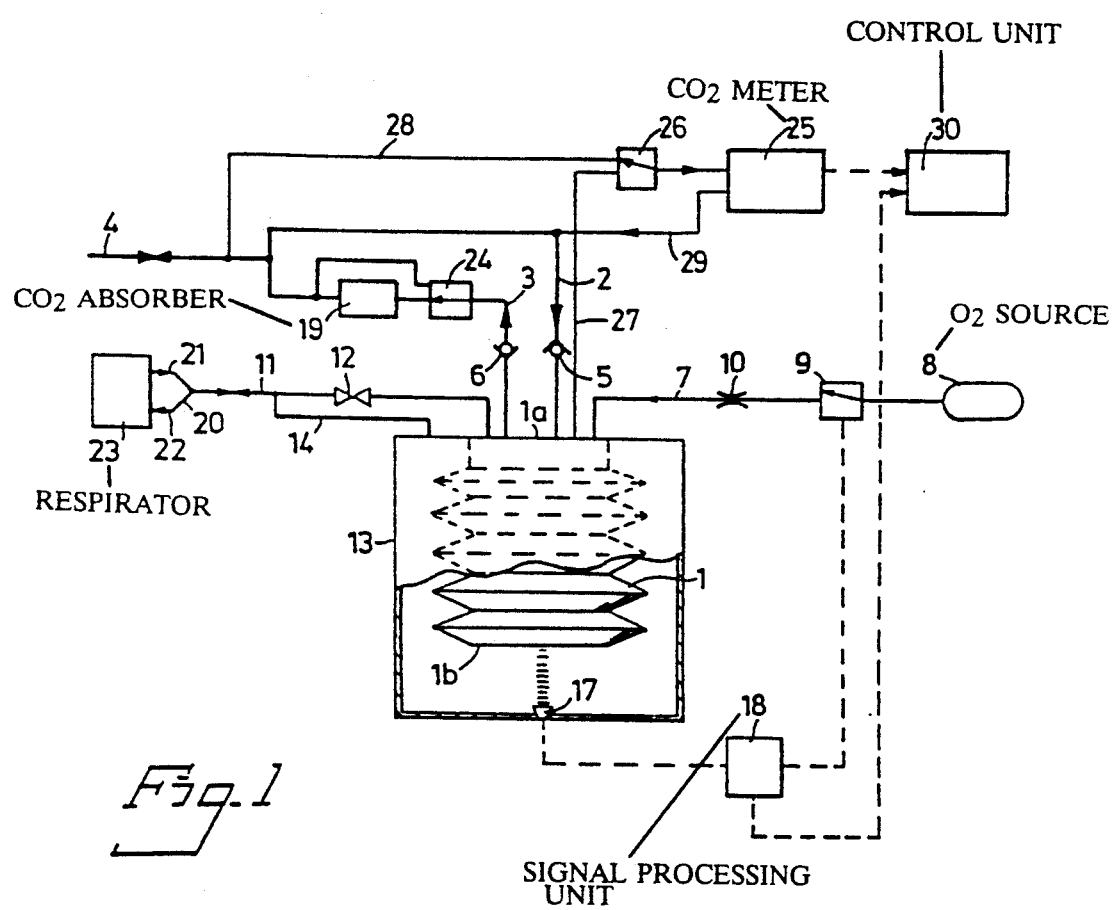
FIG. 1 is a diagrammatic illustration by way of example of an embodiment of an apparatus according to the invention.

As shown diagrammatically and by way of example in FIG. 1, an embodiment of an apparatus according to the invention comprises a reservoir 1 of variable volume. In the illustrated exemplary embodiment the reservoir is a bellows, one end wall 1a of which is fixed, while the other end wall 1b is movable in accordance with the volume variations of the reservoir 1. The maximum volume of the reservoir may be 3-5 liters.

Connected to the reservoir 1 are an inhalation conduit 3 provided with a one-way valve 6 and an exhalation conduit 2 provided with a one-way valve 5, the inhalation conduit 3 and the exhalation conduit 2 being interconnected through a common conduit 4, which is connectable, in a suitable conventional manner not illustrated, to the respiratory tract of the patient whose pulmonary function is to be examined. The two one-way valves 5 and 6 are arranged such that they permit flow of gas to the connected patient only through the inhalation conduit 3 and away from the patient only through the exhalation conduit 2.

A carbon dioxide absorber 19 can be switched into the inhalation conduit 3 by means of a controllable valve 24 to remove carbon dioxide from the respiratory gas which the connected patient inhales from the reservoir 1 through the inhalation conduit 3.

Moreover, the apparatus comprises a measuring device 25 for the determination of the concentration or partial pressure of carbon dioxide. By means of a controllable valve 26, this measuring device or meter is selectively and alternatively connectable through a narrow conduit 27 with the interior of the reservoir 1 or through a narrow conduit 28 with the conduit 4, so that by appropriate actuation of the valve 26 the measuring device or meter can measure either the carbon dioxide concentrations of the body of gas contained in the reservoir 1 or the carbon dioxide concentration of the gas flowing through the conduit 4 and breather by the connected patient. The carbon dioxide meter 25 may be of any suitable conventional type, such as an optical IR-absorption meter.

After the measurement, the gas flow which is to be measured and which is drawn into the carbon dioxide meter 25 by a pump (not shown) through the valve 26 either by way of the conduit 27 or by way of the conduit 28, is discharged through a conduit 29 to the exhalation conduit 2 and thus into the reservoir 1.

Instead of having a single carbon dioxide meter 25, the apparatus may be provided with two carbon dioxide meters permanently connected with respectively the conduit 4 and the interior of the reservoir 1. However, the provision of a single carbon dioxide meter as in the illustrated embodiment offers a significant advantage, in that any measurement errors of the carbon dioxide meter 25 substantially cancel each other and do not affect the final result.

The two valves 24 and 26 may be manually actuatable but are advantageously automatically controlled by a control and computing unit 30 forming part of the apparatus according to the invention as illustrated in the drawings.

The apparatus according to the invention also includes means for monitoring and determining the volume and the volume variations of the reservoir 1. In the illustrated embodiment, such means are in the form of a diagrammatically indicated ultrasonic distance meter 17 of suitable, conventional type which emits ultrasonic signals towards the movable end wall 1b of the bellows reservoir 1 and receives the ultrasonic signals reflected from that end wall and in a manner well known per se measures the distance between the movable end wall 1b and a stationary point. As is appreciated, the position of the movable end wall 1b varies in accordance with the variations of the volume of the reservoir 1, which volume in turn varies in accordance with the gas volumes the patient connected to the conduit 4 inhales from the reservoir 1 through the inhalation conduit 3 and then exhales into the reservoir through the exhalation conduit 2. By means a of suitable signal-processing unit 18 connected to the ultrasonic distance meter 17 it is thus possible to measure the volume of each breath (the tidal volume) and, consequently, the volume the patient breathes per unit of time (1/min), the so-called minute respirator volume, MV, or total ventilatory rate. This measured value is fed to the computing unit 30 from the signal-processing unit 18.

The carbon dioxide concentrations or carbon dioxide partial pressures measured by the carbon dioxide meter 25 are also fed to the computing unit 30.

The additional components of the exemplary embodiment which are shown in FIG. 1 represent further developments of the invention and will be described in greater detail below.

As far as it has been described so far, the illustrated apparatus is used and operates in the following manner.

The patient connected to the conduit 4, who is presupposed to be able to breathe spontaneously and unassisted, inhales from the reservoir 1 through the inhalation conduit 3 and exhales into the reservoir 1, the carbon dioxide absorber 19 being switched into the inhalation conduit 3 by means of the valve 24, so that the gas inhaled by the patient is freed from carbon dioxide. Moreover, the carbon dioxide meter 25 is connected to the conduit 27 by means of the valve 26 and is thus connected with the interior of the reservoir 1, so that the carbon dioxide meter 25 measures the concentration or partial pressure of the carbon dioxide in the reservoir 1.

Figure 2A:
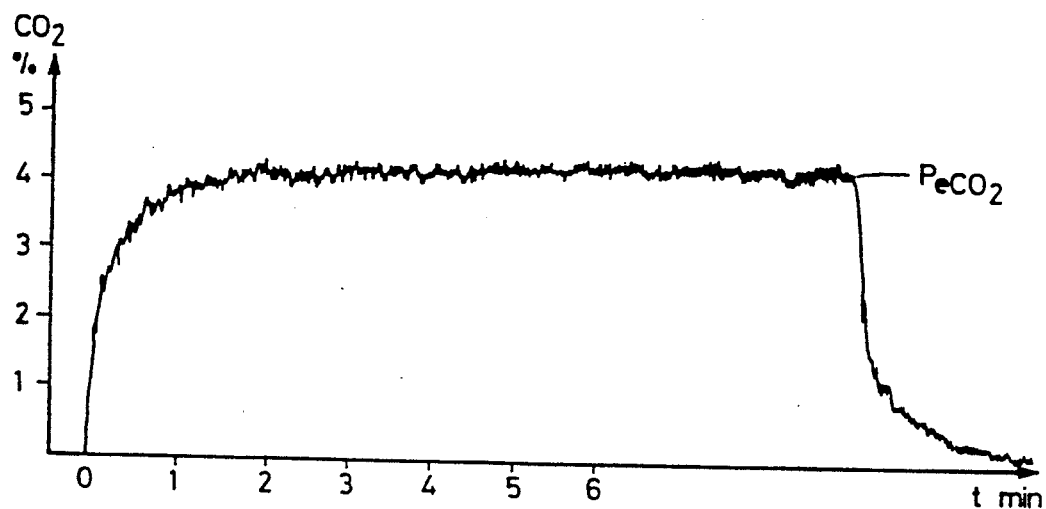
FIG. 2 and FIG. 3 are diagrams referred to in connection with the description of the mode of operation of the apparatus according to the invention which follows.

As the connected patient breathes, the exhaled gas is collected and mixed in the reservoir 1. Consequently, the carbon dioxide concentration or partial pressure in the reservoir 1 increases gradually and after a short time, on the order of 1 to 3 minutes, reaches a practically constant equilibrium valve as shown by the curve of FIG. 2a. This equilibrium value for the carbon dioxide concentration in the reservoir 1, which is measured by the carbon dioxide meter 25 through the valve 26 and the conduit 27, is the carbon dioxide concentration, $P_{eCO2}$, of the mixed exhaled respiratory gas. As is appreciated, the computing unit 30 can thus compute the amount of carbon dioxide, $V_{CO2}$, which is carried away per unit of time from the lungs of the patient with the exhaled respiratory gas, using the equation $$V_{CO2} = P_{eCO2} \times MV \qquad (1)$$

wherein MV is the minute respiratory volume of the connected patient as measured by means of the distance meter 17 and the associated signal-processing unit 18.

Obviously, the quantity of carbon dioxide thus removed from the patient's lungs with the exhaled respiratory gas has to be equal to the difference between the quantity of carbon dioxide supplied to the lungs with the venous blood and the quantity removed from the lungs with the arterial blood. It is thus possible to set up the following relationship:

$$V_{CO2} = Q \times (C_{vCO2} - C_{aCO2}) \qquad (2)$$

wherein Q is the rate of blood flow through the lungs and $C_{vCO2}$ and $C_{aCO2}$ are the amounts of carbon dioxide in respectively the venous blood and the arterial blood.

From equations (1) and (2) the following relationship can be derived:

$$Q = \frac{P_{eCO2} \times MV}{S_c \times (P_{vCO2} - P_{aCO2})} \qquad (3)$$

wherein $S_c$ is a known factor which can be determined from the slope of the carbon dioxide dissociation curve representingthe relationship between the carbon dioxide content (concentration)of the blood and the corresponding carbon dioxidepartial pressures of respectively the mixed venous blood andthe arterial blood.

Measured values representing the difference $(P_{vCO2} - P_{aCO2})$ are obtained by the apparatus according to the invention in the following manner.

When the patient is connected to the conduit 4 and the carbon dioxide absorber 19 is still switched into the inhalation conduit 3 by means of the valve 24 in the manner described above, the valve 26 is actuated such that the carbon dioxide meter 25 is connected by way of the conduit 28 to the conduit 4 and thus measures the carbon dioxide concentration or the carbon dioxide partial pressure of the respiratory gas which the patient being examined inhales and exhales.

Figure 2B:
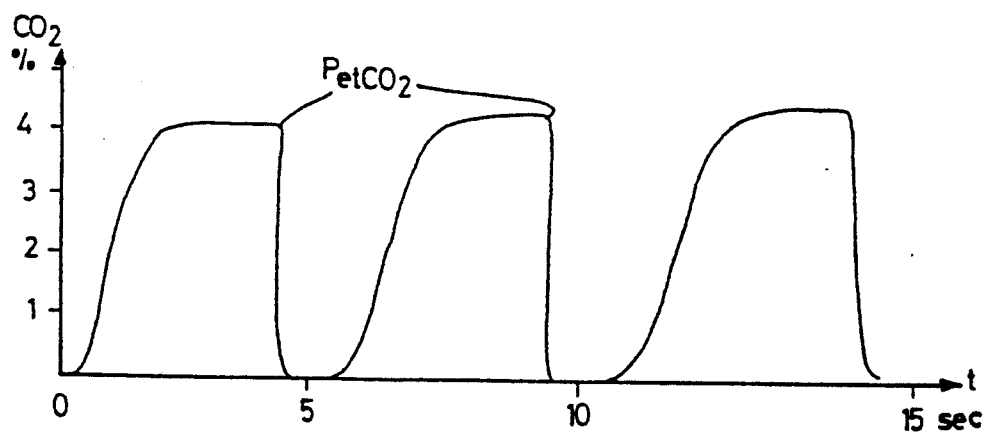

The concentration or the partial pressure of the carbon dioxide in the respiratory gas will vary as shown by the curve of FIG. 2b, that is, during each inhalation the carbon dioxide concentration is practically zero, because the carbon dioxide absorber 19 is switched into the inhalation conduit, while during each exhalation the carbon dioxide concentration of the respiratory gas increases to a maximum value, $P_{etCO2}$, the so-called end-tidal carbon dioxide partial pressure, at the end of the exhalation. This maximum carbon dioxide partial pressure of the gas exhaled at the end of each exhalation (this gas comes from the base of the lungs) may be presupposed to substantially correspond to the carbon dioxide partial pressure of the arterial blood from the lungs, that is, $P_{aCO2}$, in the case of completely healthy lungs in which there is a complete gas-exchange contact between the entire blood flow through the lungs and the respiratory gas contained in the lungs.

Thereupon the valve 24 is actuated so that the carbon dioxide absorber 19 is disconnected from the inhalation conduit 3 and no carbon dioxide is removed from the gas inhaled by the patient from the reservoir 1 through the inhalation conduit 3. The actuation of the valve 24 is effected instantaneously and preferably at the end of an exhalation.

Figure 3:
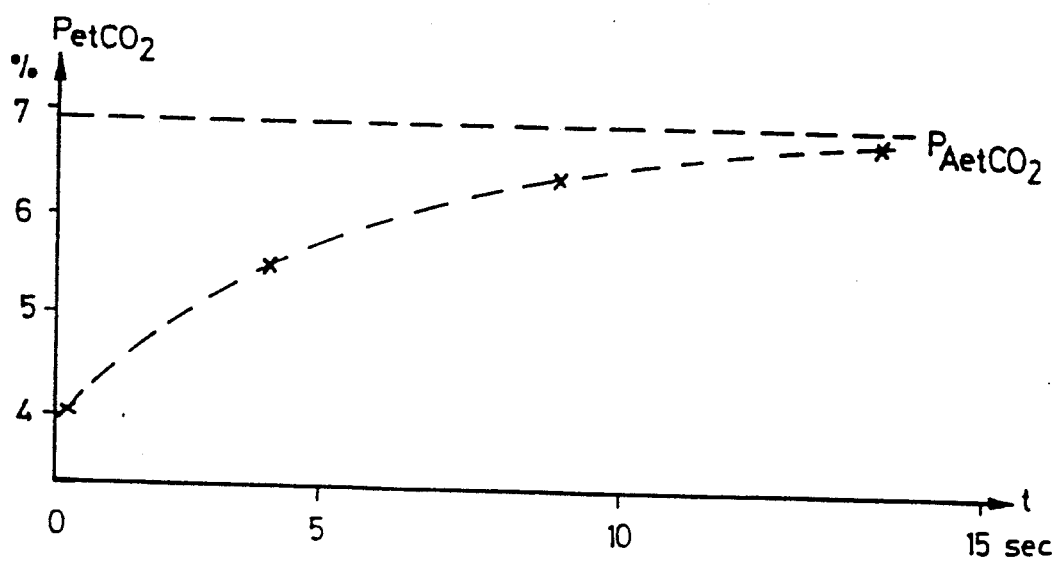

As the connected patient then continues to inhale from and exhale into the reservoir 1 with the carbon dioxide absorber 19 disconnected, the end-tidal carbon dioxide concentration, $P_{etCO2}$, as measured by the carbon dioxide meter 25 through the valve 26 and the conduit 28, of the gas exhaled through the conduit 4 by the connected patient will increase exponentially for successive breaths in the manner illustrated in FIG. 3 and approach an asymptotic value, $P_{AetCO2}$, which the calculating unit 30 can determine after a few (3-5) breathing cycles. This asymptotic value $P_{AetCO2}$ corresponds to the carbon dioxide partial pressure $P_{vCO2}$ of the mixed venous blood.

Accordingly, in the relationship (3) given above, $(P_{AetCO2}-P_{etCO2})$ can be substituted for $(P_{vCO2}-P_{aCO2})$, and, consequently, $$Q_p = \frac{P_eCO2 \times MV}{S_c \times (P_{AetCO2} - P_{etCO2})} \quad (4)$$

This will also take into account any impaired function of the lung, so that the blood flow $Q_p$ thus calculated will be a measure of the pulmonary blood flow or the lung perfusion in accordance with the definition given initially, that is, the blood flow through the lungs which is brought into gas-exchange contact with the respiratory gas contained in the lungs.

As mentioned above, the factor $S_c$ in relationship (4) is a known factor, and all other quantities are measured in the above-described manner by means of the apparatus according to the invention. Accordingly, the computing unit 30 can compute the pulmonary blood flow $q_p$ using relationship (4).

Moreover, the computing unit may be designed to compute the pulmonary volume LV for carbon dioxide using the relationship $$LV = \frac{Q_p \times S_c \times (P_B - 47)}{T} \quad (5)$$

wherein T is the time constant for the exponentially rising curve in FIG. 3 and $P_B$ is the atmospheric pressure. It should be noted in this connection that the pulmonary volume LV for carbon dioxide which is computed in this manner is not identical with the gas-filled volume of the lungs, as some carbon dioxide is dissolved in the lung tissue.

In accordance with an advantageous further feature of the invention, the apparatus may comprise a device for controllable supply of pure oxygen to the reservoir 1 through a conduit 7 as shown in FIG. 1. This device may include a suitable, constant-pressure oxygen source 8 (not shown in detail) which may be connected with the conduit 7 and thus with the reservoir 1 by way of a controllable on-off valve 9 and a restriction 10. While the patient connected to the conduit 4 is being examined in the above-described manner, the valve 9 is controlled from the signal-processing unit 18 associated with the ultrasonic distance meter 17 such that a sufficient amount of pure oxygen is supplied to the reservoir 1 through the conduit 7 to ensure that the volume of the reservoir 1 is substantially the same at a given point in each breathing cycle, preferably at the end of each exhalation, i.e., when the reservoir 1 has its largest volume.

In this manner, the volume of oxygen thus supplied to the reservoir 1 will correspond to the amount of oxygen consumed by the patient being examined, and this consumed oxygen amount $V_{O2}$ can readily be determined by measuring the amount of oxygen supplied to the reservoir 1 through the conduit 7. This can be done by causing the unit 18 controlling the valve 9 to measure in a suitable manner the time during which the valve 9 is kept open and to feed the measured $V_{O2}$ to the computing unit 30.

Using the value $V_{O2}$ of the oxygen consumption of the patient being examined, the computing unit 30 can compute the patient's respiratory quotient RQ using the relationship $$RQ = \frac{V_{CO2}}{V_{O2}} = \frac{P_eCO2 \times MV}{V_{O2}} \quad (6)$$

Because, moreover, the above-described principle for the carbon dioxide balance across the lungs can also be applied to the oxygen balance, it is possible in analogy with relationship (2) given above to set up the relationship $$Q = \frac{V_{O2}}{C_{aO2} - C_{vO2}} \quad (7)$$

wherein $C_{aO2}$ and $C_{vO2}$ are respectively the oxygen content in the arterial blood and the oxygen content in the mixed venous blood.

The relationship of the oxygen content $C_{O2}$ with the oxygen saturation $S_{O2}$ of the blood and the oxygen partial pressure $P_{O2}$ is expressed by the known relationship $$C_{O2} = S_{O2} \times Hb \times 1.34 + 0{,}0029\, P_{O2} \quad (8)$$

which of course is valid for both arterial blood and venous blood. Assuming that the last small correctional term has normal physiological values, it is thus possible to use relationship (8) for setting up the following relationship $$S_{vO2} = S_{aO2} - 100 \times \frac{(C_{aO2} - C_{vO2}) - 0{,}174}{1{,}34 \times Hb} \quad (9)$$

wherein $S_{vO2}$ and $S_{aO2}$ represent the oxygen saturation, expressed as a percentage, in respectively mixed venous blood and arterial blood.

Using relationships (4) and (7), the term $(C_{aO2}-C_{vO2})$ in relationship (9) can be replaced with a term which only includes the parameters measured in the above-described manner by means of the apparatus according to the invention. Such substitution yields the relationship $$S_{vO2} = 98 - 100 \times \frac{\frac{S_c \times (P_{AetCO2} - P_{etCO2}) \times V_{O2}}{P_eCO2 \times MV} - 0{,}174}{1{,}34 \times Hb} \quad (10)$$

wherein the oxygen saturation $S_{vO2}$ of the mixed venous blood is expressed as a percentage and the oxygen saturation $S_{aO2}$ of the arterial blood is set at 98% for a healthy person.

If the oxygen saturation of the arterial blood $S_{aO2}$ of the patient being examined is measured separately in a suitable known manner, such as non-invasively by means of a pulse oximeter, and the measured value is supplied to the computing unit 30, the blood flow Q discharged from the heart of the patient being examined, the so-called minute cardiac volume or cardiac output, can be calculated using the relationship $$Q = \frac{Q_p \times (98 - S_{vO2})}{(S_{aO2} - S_{vO2})} \quad (11)$$

wherein $Q_p$ is obtained from (4) and $S_{vO2}$ is obtained from (10).

In the foregoing description it has been presupposed that the patient being examined is capable of breathing spontaneously without any assistance. In order that the apparatus may also be used for a patient who is not capable of breathing unassisted in a satisfactory manner and who has therefore to be connected with a respirator to get the required breathing assistance, the apparatus according to the invention may advantageously be provided with additional components as shown in FIG. 1. These additional components include a rigid sealed vessel 13 of constant volume which encloses the variable reservoir 1.

Moreover, the interior of the reservoir 1 is connected to a conduit 11 which includes a shut-off valve 12 and which is connected through a conventional, only diagrammatically shown Y-connector 20 with the inhalation and exhalation conduits 21, 22 of a respirator 23 which is used to provide breathing assistance to the patient being examined.

In addition, the interior of the outer, rigid casing 13 is connected with a conduit 14 which is connected with the conduit 11 such that it is in constant communication with the inhalation and exhalation conduits 21, 22 of the respirator 23.

When no measurement is being carried out on the patient connected with the conduit 4, the shut-off valve 12 of the conduit 11 is held open, so that the patient is connected with the respirator through the reservoir 1 and receives both the required respiratory gas and the required breathing assistance from the respirator. While measurement is carried out on the patient in the manner described above, the valve 12 is kept closed, so that the patient breathes only from and into the reservoir 1. However, the patient still gets the required breathing assistance from the respirator 23 as a consequence of the pressure in the outer rigid casing 13 surrounding the variable reservoir 1 varying at the pace of operation of the respirator 23. If the patient connected to the apparatus does not meet breathing assistance, but can breathe himself, the conduit 11 is simply disconnected from the respirator 23 and caused to communicate with the ambient atmosphere.

As is apparent from the foregoing description, several additional different embodiments and modifications of the apparatus according to the invention are possible within the scope of the invention. For example, the reservoir 1 which is variable in respect of its volume may be designed in several different ways, as may the means for the selective connection of the carbon dioxide absorber and the carbon dioxide meter. Naturally, the means for monitoring the volume of the reservoir 1 may also be designed in several different ways.

We claim:

1. Apparatus for examining and measuring the pulmonary function of a patient, comprising
   (a) a sealed reservoir (1) having an interior of variable volume,
   (b) an inhalation conduit (3) and an exhalation conduit (2), which are connected with the reservoir (1) and include one-way valve means (5,6) permitting flow of gas through the inhalation conduit only in the direction from the reservoir and permitting flow of gas through the exhalation conduit only in the direction toward the reservoir,
   (c) first connecting means (4) for connecting the inhalation conduit (3) and the exhalation conduit (2) with the respiratory tract of a patient to be examined, such that the patient can inhale from the reservoir (1) through the inhalation conduit and exhale into the reservoir through the exhalation conduit,
   (d) carbon dioxide adsorbing means (19) for removing carbon dioxide from a stream of gas flowing through the inhalation conduit (3),
   (e) monitoring means (17,18) for monitoring volumetric variations of the reservoir (1) resulting from the inhalation and exhalation of the patient and for determining the patient's total ventilatory rate, characterized by means (24) for selectively switching the carbon dioxide absorbing means (19) into the inhalation conduit (3), concentration measuring means (25) for measuring the carbon dioxide concentration of a gas mixture, second connecting means (26) for connecting the concentration measuring means (25) with the interior of the reservoir (1) and with the first connecting means (4), and a computing unit (3) which is connected with the concentration measuring means (25) and with the monitoring means (17,18) and which comprises computing means for computing the pulmonary blood flow $Q_p$ of the patient essentially in accordance with the equation $$Q_p = \frac{P_{eCO2} \times MV}{S_c \times (P_{AetCO2} - P_{etCO2})} \quad (4)$$

wherein

MV is the patient's total ventilatory rate, $P_{aCO2}$ is the carbon dioxide concentration in the reservoir (1) at equilibrium, when the patient inhales from and exhales into the reservoir (10 with the carbon dioxide absorbing means (19) switched into the inhalation conduit (3), $P_{etCO2}$ is the carbon dioxide concentration of the gas exhaled by the patient at the end of an exhalation with the carbon dioxide absorbing means (19) switched into the inhalation conduit (3), $P_{AstCO2}$ is the asymptotic value which the carbon dioxide concentration of the gas exhaled by the patient approaches at the end of each exhalation when the patient inhales from and exhales into the reservoir (1) with the carbon dioxide absorbing means (19) disconnected from the inhalation conduit (3), and $S_c$ is a known constant.

2. Apparatus according to claim 1, characterized in that the concentration measuring means (25) is selectively and alternatively connectable with the interior of the reservoir (1) and with the first connecting means (4).

3. Apparatus according to claim 2, characterized in that the computing unit (30) comprises means for computing a carbon dioxide removal $V_{CO2}$ from the patient's lungs essentially in accordance with the equation $$V_{CO2} = P_{eCO2} \times MV \quad (1)$$

4. Apparatus according to claim 3, characterized in that the computing unit (30) comprises means for computing the patient's pulmonary volume LV for carbon dioxide essentially in accordance with the equation $$LV = \frac{Q_p \times S_c \times (P_B - 47)}{T} \quad (5)$$

wherein

T is a time constant for the exponential increase of $P_{etCO2}$ when the patient inhales from and exhales into the reservoir (1) with the carbon dioxide absorbing means (19) disconnected from the inhalation conduit (3), and $P_B$ is the atmospheric pressure.

5. Apparatus according to claim 4, characterized in that it comprises means (8,9,10) controlled by the monitoring means (17,18) for feeding pure oxygen to the reservoir (1) in such quantities that the reservoir volume is substantially the same at a given point in each breathing cycle of the patient, and means (18) for measuring a quantity $V_{O2}$ of oxygen fed to the reservoir (1) per unit of time.

6. Apparatus according to claim 3, characterized in that it comprises means (8,9,10) controlled by the monitoring means (17,18) for feeding pure oxygen to the reservoir (1) in such quantities that the reservoir volume is substantially the same at a given point in each breathing cycle of the patient, and means (18) for measuring a quantity $V_{O2}$ of oxygen fed to the reservoir (1) per unit of time.

7. Apparatus according to claim 6, characterized in that it additionally comprises an outer rigid fixed-volume casing (13) sealingly enclosing the reservoir (1), a connecting conduit (14) for constantly connecting an interior of the rigid casing with respirator (23) inhalation and exhalation conduits (21,22) respectively discharging and receiving respiratory gas, and a connecting conduit (11) comprising shut-off means (12) for connecting the interior of the reservoir (1) with the respirator (23) inhalation and exhalation conduits (21,22).

8. Apparatus according to claim 2, characterized in that the computing unit (30) comprises areas for computing the patient's pulmonary volume LV for carbon dioxide essentially in accordance with the equation $$LV = \frac{Q_p \times S_c \times (P_B - 47)}{T} \quad (5)$$

wherein

T is a time constant for the exponential increase of $P_{etCO2}$ when the patient inhales from and exhales into the reservoir (1) with the carbon dioxide absorbing means (19) disconnected from the inhalation conduit (3), and $P_B$ is the atmospheric pressure.

9. Apparatus according to claim 8, characterized in that it comprises means (8,9,1) controlled by the monitoring means (17,18) for feeding pure oxygen to the reservoir (1) in such quantities that the reservoir volume is substantially the same at a given point in each breathing cycle of the patient, and means (18) for measuring a quantity $V_{O2}$ of oxygen fed to the reservoir (1) per unit of time.

10. Apparatus according to claim 2, characterized in that it comprises means (8,9,10) controlled by the monitoring means (17,18) for feeding pure oxygen to the reservoir (1) in such quantities that the reservoir volume is substantially the same at a given point in each breathing cycle of the patient, and means (18) for measuring a quantity $V_{O2}$ of oxygen fed to the reservoir (1) per unit of time.

11. Apparatus according to claim 5, characterized in that the computing unit (30) comprises means for computing a respiratory quotient RQ substantially in accordance with the equation $$RQ = \frac{V_{CO2}}{V_{O2}} = \frac{P_{eCO2} \times MV}{V_{O2}} \quad (6)$$

12. Apparatus according to claim 11, characterized in that the computing unit (30) comprises means to compute oxygen saturation of mixed venous blood of the patient substantially in accordance with the equation $$S_{vO2} = 98 - 100 \times \frac{\frac{S_c \times (P_{AetCO2} - P_{etCO2}) \times V_{O2}}{P_{eCO2} \times MV}}{1.34 \times Hb} - 0.174 \quad (10)$$

wherein Hb is the patient's hemoglobin concentration and the oxygen saturation of arterial blood is presupposed to be 98 percent for a healthy person.

13. Apparatus according to claim 12, characterized in that it additionally comprises an outer rigid fixed-volume casing (13) sealingly enclosing the reservoir (1), a connecting conduit (14) for constantly connecting an interior of the rigid casing with respirator (23) inhalation and exhalation conduits (21,22) respectively discharging and receiving respiratory gas, and a connecting conduit (11) comprising shut-off means (12) for connecting the interior of the reservoir (1) with the respirator (23) inhalation and exhalation conduits (21,22).

14. Apparatus according to claim 11, characterized in that the computing unit (30) comprises means to compute cardiac output Q of the patient substantially in accordance with the equation $$Q = \frac{Q_p \times (98 - S_{vO2})}{(S_{aO2} - S_{vO2})} \quad (11)$$

wherein $S_{aO2}$ is oxygen saturation of arterial blood of the patient as measured separately.

15. Apparatus according to claim 14, characterized in that it additionally comprises an outer rigid fixed-volume casing (13) sealingly enclosing the reservoir (1), a connecting conduit (14) for constantly connecting an interior of the rigid casing with respirator (23) inhalation and exhalation conduits (21,22) respectively discharging and receiving respiratory gas, and a connecting conduit (11) comprising shut-off means (12) for connecting the interior of the reservoir (1) with the respirator (23) inhalation and exhalation conduits (21,22).

16. Apparatus according to claim 10, characterized in that the computing unit (30) comprises means to compute oxygen saturation of mixed venous blood of the patient substantially in accordance with the equation $$S_{vO2} = 98 - 100 \times \frac{\frac{S_c \times (P_{AetCO2} - P_{etCO2}) \times V_{O2}}{P_{eCO2} \times MV}}{1.34 \times Hb} - 0.174 \quad (10)$$

wherein Hb is the patient's hemoglobin concentration and the oxygen saturation of arterial blood is presupposed to be 98 percent for a healthy person.

17. Apparatus according to claim 16, characterized in that the computing unit (30) comprises means to compute cardiac output Q of the patient substantially in accordance with the equation $$Q = \frac{Q_p \times (98 - S_{vO2})}{(S_{aO2} - S_{vO2})} \quad (11)$$

wherein $S_{aO2}$ is oxygen saturation of arterial blood of the patient as measured separately.

18. Apparatus according to claim 10, characterized in that the computing unit (30) comprises means to compute cardiac output Q of the patient substantially in accordance with the equation $$Q = \frac{Q_p \times (98 - S_{vO2})}{(S_{aO2} - S_{vO2})} \quad (11)$$

wherein $S_{aO2}$ is oxygen saturation of arterial blood of the patient as measured separately.

19. Apparatus according to claim 2, characterized in that it additionally comprises an outer rigid fixed-volume casing (13) sealingly enclosing the reservoir (1), a connecting conduit (14) for constantly connecting an interior of the rigid casing with respirator (23) inhalation and exhalation conduits (21,22) respectively discharging and receiving respiratory gas, and a connecting conduit (11) comprising shut-off means (12) for connecting the interior of the reservoir (1) with the respirator (23) inhalation and exhalation conduits (21,22).

20. Apparatus according to claim 1, characterized in that it additionally comprises an outer rigid fixed-volume casing (13) sealingly enclosing the reservoir (1), a connecting conduit (14) for constantly connecting an interior of the rigid casing with respirator (23) inhalation and exhalation conduits (21,22) respectively discharging and receiving respiratory gas, and a connecting conduit (11) comprising shut-off means (12) for connecting the interior of the reservoir (1) with the respirator (23) inhalation and exhalation conduits (21,22).

* * * * *